United States Patent [19]

Watson

[11] Patent Number: Plant 6,041

[45] Date of Patent: Oct. 20, 1987

[54] AMELANCHIER NAMED "PRINCESS DIANA"

[76] Inventor: Thomas Watson, 1746 Hwy. 73, Cambridge, Wis. 53523

[21] Appl. No.: 705,617

[22] Filed: Feb. 26, 1985

[51] Int. Cl.[4] ..... A01H 5/00
[52] U.S. Cl. ..... Plt./51
[58] Field of Search ..... Plt./51

[56] References Cited

U.S. PATENT DOCUMENTS

P.P. 3,092 4/1972 Flemer ..... Plt. 51
P.P. 5,717 4/1986 Wandell ..... Plt. 51

OTHER PUBLICATIONS

DeWolf, Gordon, "Shadbush", *Horticulture,* vol. 60, No. 5, p. 22, May 1982.

Weaver, Richard E., Jr., "The Shadbushes", *Arnoldia,* vol. 34, No. 1 (1975), p. 21–31.

Wyman, D., *Shrubs and Vines for American Gardens,* MacMillan Publishing Co. Inc., N.Y. 1973, p. 119 only.

Hillier, H. G., *Hillier's Manual of Trees and Shrubs,* Pub. A. S. Barnes and Company, 1979, p. 31 only.

Rehder, A., *Manual of Cultivated Trees and Shrubs,* MacMillan & Company, N.Y., 1960, p. 388 only.

Fernald, M. L., *Manual of Botany,* American Book Company, 1950, pp. 766 and 767 only.

*Primary Examiner*—James R. Feyrer

*Attorney, Agent, or Firm*—Isaksen, Lathrop, Esch, Hart & Clark

[57] ABSTRACT

A new variety of *Amelanchier grandiflora* is disclosed which is characterized by its unique yellow flower buds unfold into white flowers, its wide-spread branches, and, most particularly, by a brilliant red fall foliage display.

3 Drawing Figures

The present invention relates to a new and distinct variety of *Amelanchier grandiflora* which was found in a cultivated area.

The distinct characteristics of the tree of the present invention are that white flowers unfold from yellow-tinged flower buds, the fall foliage is a brilliant red color, and the branches are very wide-spread. These characteristics are significantly different from other varieties of *Amelanchier grandiflora.*

Asexual reproduction of the new variety was accomplished by tissue culture of new bud cells, and showed that the foregoing characteristics and distinctions come true to form and are established and transmitted through succeeding propagations.

The accompanying drawing shows a typical tree specimen of the new variety, together with typical foliage and flower specimens on a larger scale.

The following is a detailed description of the new variety, with color terminology in accordance with the Inter-Society Color Council — National Bureau of Standards Circular 553 Color Chart, except where general color terms of ordinary dictionary significance are obvious.

Parentage: Bud cells.

*Seed parents.*—Parents unknown but plant believed to be a cross between *Amelanchier laevis* and *Amelanchier arborea.* The female parent was naturally pollinated.

Propagation: Holds its distinguishing characteristics through succeeding propagations by tissue culture.

Locality where discovered: Cultivated yard in Elm Grove, Wis.

Locality where propagated and grown: Cambridge, Wis.

Tree: Slender, upright, grows to an average of 20–25 feet tall. The specimen shown in the photograph was only three years old at the time of photograph. Mature trees are generally over twenty feet in height.

Trunk: Slender; tree-like and 1 to 5 in number; smooth.

*Color.*—Brown-Gray, Hue No. 64.

Branches: Slender, smooth.

*Spreading habit.*—color — Gray Brown, Hue No. 61.

Foliage:

*Leaves.*—Thick.

*Quantity.*—Moderate.

*Length.*—Average 7 cm.

*Width.*—Average 4 cm.

*Shape.*—Oval-lanceolate.

*Color.*—Upper surface — medium olive green, Hue No. 125. Under surface — deep yellow green, Hue No. 118. Fall coloration — deep red orange, Hue No. 36.

*Margin.*—Serrate; serrations about 2 mm deep and average 0.3 cm apart.

*Petiole.*—Average 2 cm long. Unfolding new leaves are moderately pubescent underside and red-bronze in color close to Hue No. 55.

Flower buds:

*Hardiness.*——30° F.

*Size.*—Length average 1.0 cm. Width average 0.4 cm.

*Shape.*—Globular.

*Color.*—Pale Yellow; Hue No. 89.

Flowers:

*Quantity.*—Abundant average April 15, Zone 4.

*Size.*—average 2 cm in diameter. Flowers grouped in horizontal clusters.

*Petalage.*—5 petals. Shape — round. Size: average 0.6 cm width; average 1.2 cm long. Color White; Hue No. 263.

Fruits:

*Borne.*—Average June 15, Zone 4. Abundant.

*Shape.*—Globular.

*Size.*—Length average 0.8 cm. Width average 0.9 cm.

*Color.*—Bluish deep purple, Hue No. 225.

Winter buds: Narrow, pointed, light brown, Hue No. 58.

I claim:

1. A new and distinct variety of *Amelanchier grandiflora* substantially as herein shown and described, characterized particularly as to novelty by its unique yellow flower buds which unfold to white flowers, brilliant red fall foliage, and wide-spread branches.

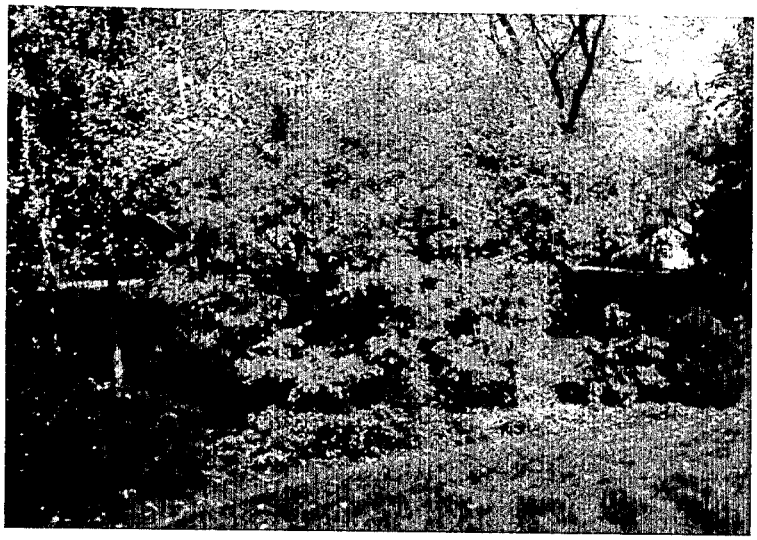
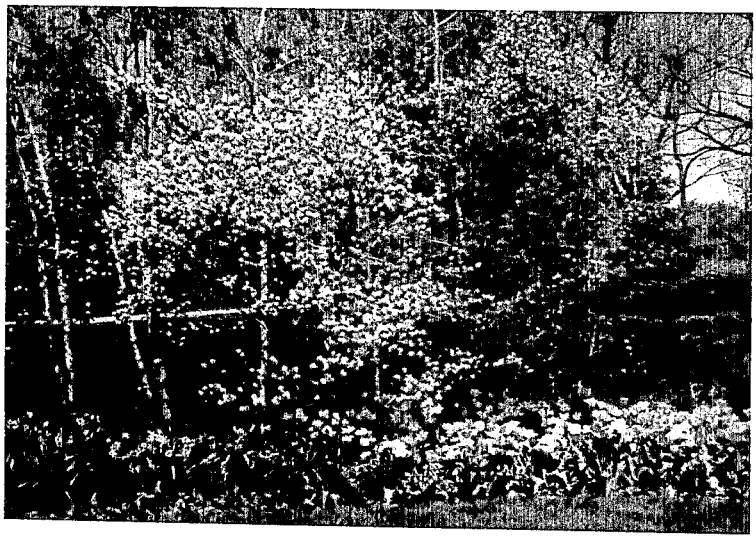
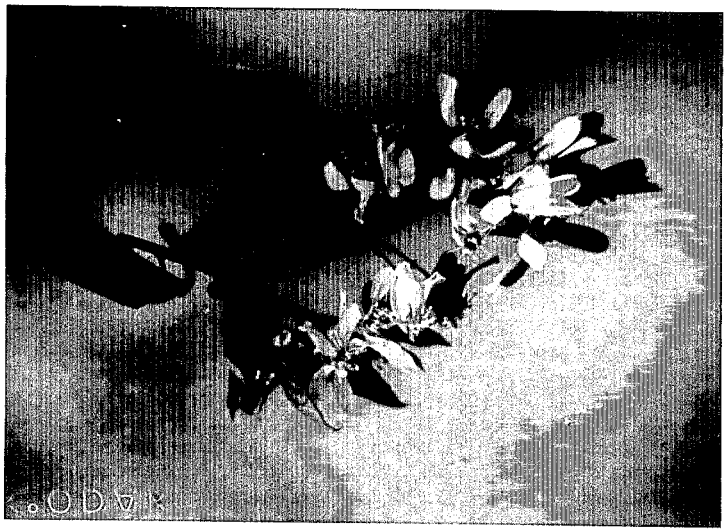

* * * * *